(12) United States Patent
Castro

(10) Patent No.: US 8,084,202 B2
(45) Date of Patent: Dec. 27, 2011

(54) OPTICAL DETECTION FOR ELECTRONIC MICROARRAYS

(75) Inventor: Hernan A. Castro, Shingle Springs, CA (US)

(73) Assignee: Intel Corporation, Santa Clara, CA (US)

( * ) Notice: Subject to any disclaimer, the term of this patent is extended or adjusted under 35 U.S.C. 154(b) by 412 days.

(21) Appl. No.: 12/059,833

(22) Filed: Mar. 31, 2008

(65) Prior Publication Data

US 2009/0247418 A1    Oct. 1, 2009

(51) Int. Cl.
*C12Q 1/68* (2006.01)
*C12M 1/38* (2006.01)
*C12M 3/00* (2006.01)
*C07H 21/02* (2006.01)
*C07H 21/04* (2006.01)

(52) U.S. Cl. .......... 435/6.1; 435/6; 435/287.2; 536/23.1

(58) Field of Classification Search ........... 435/6, 287.2; 536/23.1
See application file for complete search history.

(56) References Cited

U.S. PATENT DOCUMENTS

| | | | |
|---|---|---|---|
| 5,667,667 A * | 9/1997 | Southern | 205/687 |
| 6,309,833 B1 * | 10/2001 | Edman et al. | 435/6 |
| 2005/0181409 A1 * | 8/2005 | Park et al. | 435/6 |
| 2006/0105373 A1 * | 5/2006 | Pourmand et al. | 435/6 |

OTHER PUBLICATIONS

Reynolds et al, Homogeneous nanoparticle based quantitative colrimatric detection of oligonucleotides, 2000, J. Am. Chem. Soc., 122, 3795-3796.*
Reynolds et al -Supplemental section 2000, J. Am. Chem. Soc., 122, pp. 1-6.*

* cited by examiner

*Primary Examiner* — Stephen Kapushoc
*Assistant Examiner* — Narayan Bhat
(74) *Attorney, Agent, or Firm* — Julia A. Hodge

(57) ABSTRACT

Embodiments of the invention provide methods for detecting molecular recognition events electronically and optically. Methods according to embodiments of the invention provide a nucleic acid molecule that hybridizes to a first probe nucleic acid molecule attached to an electronic detector wherein the second nucleic acid molecule comprises two regions. The two regions of the second nucleic acid molecule consist of a region that is complementary to the probe nucleic acid and a distal region that is not complementary to the first probe nucleic acid molecule. The hybridization reaction is detected electronically. A third nucleic acid molecule having an attached optically detectable label is hybridized to the distal region of the second nucleic acid molecule and the label is detected optically. Methods according to embodiments of the invention are useful, for example, to validate and quantify electronic detection methods.

15 Claims, 6 Drawing Sheets

OPTICAL DETECTION FOR ELECTRONIC MICROARRAYS

CROSS REFERENCE TO RELATED APPLICATIONS

The present application is related to U.S. patent application Ser. No. 11/646,602, entitled "Method and Apparatus for Combined Electrochemical Synthesis and Detection of Analytes," filed Dec. 28, 2006, now pending, U.S. patent application Ser. No. 11/646,615, entitled "Method and Apparatus for Match Quality Analysis of Analyte Binding," filed Dec. 28, 2006, now pending, and U.S. patent application Ser. No. 11/646,600, entitled "Quality Control Methods for the Manufacture of Polymer Arrays" filed Dec. 28, 2006, now pending, the disclosures of which are considered part or and are incorporated by reference in the disclosure of this application.

BACKGROUND OF THE INVENTION

1. Field of the Invention

The embodiments of the present invention relate generally to methods for monitoring the synthesis of polymers on an array, molecular recognition reactions, and to electrochemical polymer synthesis and detection devices.

2. Background Information

Microarrays of nucleic acids, peptides, proteins, and oligosaccharides continue to gain importance as powerful tools for research and diagnostic applications in the biomedical sciences. Nucleic acid microarrays, for example, can be used to monitor gene expression and genetic mutations in a massively parallel manner. Proteinaceous microarrays provide the ability, for example, to characterize the molecular progression of disease, research cellular pathways, and perform high throughput screening in drug discovery applications. The ability to collect large volumes of information is an integral part of biomarker discovery and personalization of medical treatments. Further, other applications in bioscience, such as for example, the analysis of the proteomic content of an organism, disease detection, pathogen detection, environmental protection, food safety, and biodefense are capable of benefiting from tools that allow rapid multiplexed interrogation of analyte samples.

Genetic information in living organisms is contained in the form of very long nucleic acid molecules such as deoxyribonucleic acid (DNA) and ribonucleic acid (RNA). Naturally occurring DNA and RNA molecules are typically composed of repeating chemical building blocks called nucleotides which are in turn made up of a sugar (deoxyribose or ribose, respectively), a phosphate group, and one of five bases, adenine (A), cytosine (C), guanine (G), and thymine (T) or uracil (U). The human genome, for example, contains approximately three billion nucleotides of DNA sequence and an estimated 20,000 to 25,000 genes. DNA sequence information can be used to determine multiple characteristics of an individual as well as the presence of and or susceptibility to many common diseases, such as cancer, cystic fibrosis, and sickle cell anemia.

As the genomic and proteomic knowledge base expands, so does the need for methods to collect, understand, and apply biologically relevant information. The drive towards personalized medicine magnifies these needs. Methods, such as analyses using microarrays that allow the use of small volumes of sample for highly multiplexed analysis of a plurality of components are valuable tools. Methods that provide for the controllable automated manufacture of arrays derive value from these same biomedical detection and analysis goals.

DETAILED DESCRIPTION OF THE INVENTION

Embodiments of the invention provide methods for electrically and optically monitoring the synthesis of polymers on a substrate and methods for electrically and optically monitoring the molecular recognition reactions of polymers on a substrate. In embodiments of the invention, the solid support comprises an array of regions in which polymers may be synthesized or attached and electrically and optically detected. Polymers can either be synthesized in situ on the surfaces of devices comprising an array of electronic polymer detection devices or an array of polymers that is attached to the surfaces of the array of devices can be created by spotting techniques, for example. Methods for optical and electronic detection are provided in which the optical monitoring of events occurring on the polymer array does not interfere with the electronic detection of events on the surface of the electronic detection device.

Methods according to embodiments of the invention are useful, for example, to validate and quantify electronic detection methods. Detection of an optical signal from a label molecule attached to the surface of the substrate indicates that a hybridization reaction has occurred and the intensity of the signal is optionally used to quantify the amount of hybridization using known properties of the label molecule (such as label signal intensity versus concentration). In addition, methods according to embodiments of the invention can be used to develop functionalization and hybridization protocols for electrical detection and synthesis of polymers on a substrate.

Figure 1:
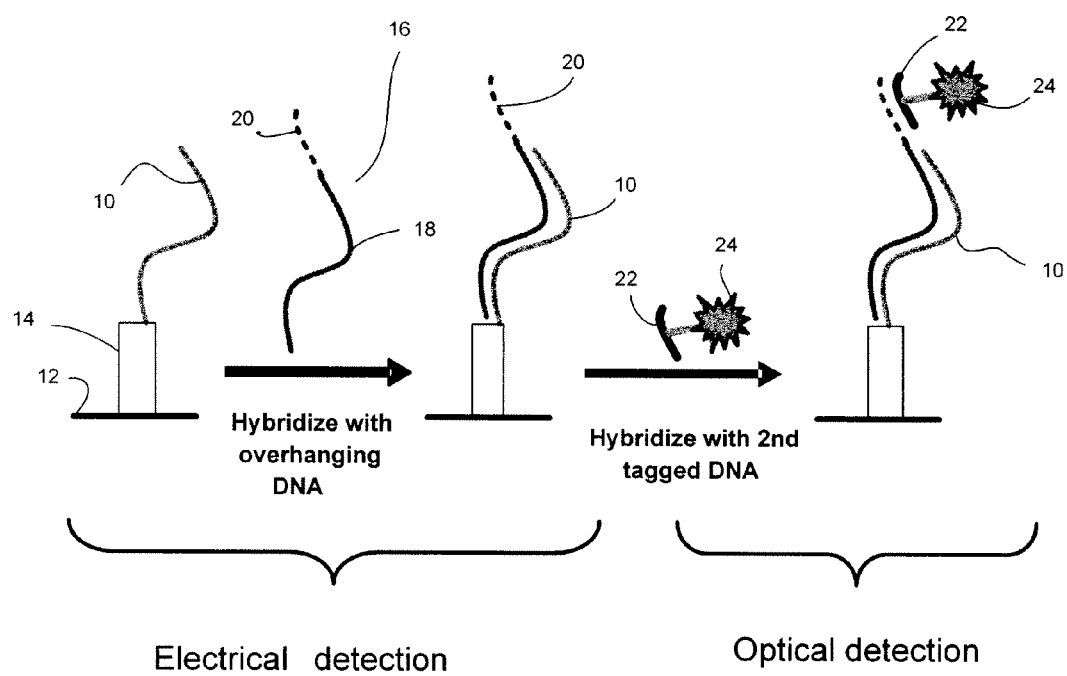
FIG. 1 provides a schematic diagram showing a method for the electrical detection of a molecular recognition reaction in conjunction with the optical detection of the molecular recognition reaction.

FIG. 1 schematically diagrams a method for detecting a molecular recognition event for a polymer attached to a substrate. In FIG. 1, a DNA strand 10 is attached to a substrate 12 through a linking molecule 14. A solution containing a second complementary DNA molecule 16 is provided to the substrate surface under conditions that allow the second DNA molecule 16 to hybridize to the first DNA molecule 10. The second DNA molecule 16 has two regions, a first complementary region 18 is complementary to the second DNA strand, and a second overhang region 20 remains single stranded after the second DNA strand 16 hybridizes to the surface-attached first DNA molecule 10. The overhang region 20 remains available for hybridization to a third complementary DNA sequence after the first hybridization reaction. The third complementary DNA sequence 22 is complementary to the overhang region 20. The first hybridization reaction is detected electrically. The first hybridization reaction can then also be verified optically through a second hybridization reaction. A third DNA molecule 22 having a sequence that is complementary to the overhang region 20 of the second DNA molecule 16 and having an optically detectable label 24 attached is hybridized to the overhang region 20. The label 24 is then detected optically. Advantageously, the optically detectable label is not present during the electrical detection of the hybridization reaction and therefore does not interfere with the detection of the hybridization reaction.

Electrical detection of an unlabeled polymer or molecular recognition event on a surface is uncomplicated by effects caused by the presence of the label. Thus embodiments of the invention provide methods that allow for simplified electronic detection of molecules and molecular recognition events while also providing the ability to detect the molecule or probe on the surface through optical methods. Optical detection of probes and molecules on a surface can be valuable methods for determining the existence, fidelity, and or density of molecules on a surface. If an array of probes has been synthesized in situ on the surface of the chip, it can be valuable to determine if the synthesis occurred as planned or if errors were introduced into the process. For example, hybridization reactions performed at more than one stringency condition can reveal whether or not the sequence of the probes on the surface is the anticipated sequence and aid in quantifying the degree of error in the sequence of the synthesized probes. Mismatched bases in hybridization reactions reduce the stability of the hybridized duplex and cause the double-stranded hybridization product to unhybridize more easily. A mismatched pair of nucleic acids will unhybridize more easily (for example, at a lower temperature) than the corresponding fully complementary pair of nucleic acids.

An array is an intentionally-created collection of molecules housed on a solid support in which the identity or source of a group of molecules is known based on its location on the array. The molecules housed on the array and within a feature of an array can be identical to or different from each other. A macroarray generally contains feature sizes of about 300 μm or larger and can be imaged by gel and blot scanners. A micro array generally has feature sizes of less than 300 μm.

The features, regions, spots, or sectors of an array may have any convenient shape, for example, circular, square, rectangular, elliptical, or wedge-shaped. In some embodiments, the region in which each distinct molecule is synthesized within a sector is smaller than about 1 mm$^2$ or less than 0.5 mm$^2$. In further embodiments the regions have an area less than about 10,000 μm$^2$ or less than 2.5 μm$^2$. Additionally, multiple copies of a polymer are located within any region. The number of copies of a polymer can be in the thousands to the millions within a region. In general, an array can have any number of features, and the number of features contained in an array may be selected to address such considerations as, for example, experimental objectives, information-gathering objectives, and cost effectiveness. An array could be, for example, a 20×20 matrix having 400 regions, 64×32 matrix having 2,048 regions, or a 640×320 array having 204,800 regions. Advantageously, the present invention is not limited to a particular size or configuration for the array.

As used in the specification and claims, the singular forms "a," "an," and "the" include plural references unless the context clearly indicates otherwise. For example, the term "an array" may include a plurality of arrays unless the context clearly indicates otherwise.

A solid support, support, or substrate is an object having a rigid or semi-rigid surface or surfaces. In some aspects at least one surface of a solid support is planar or substantially planar. In other embodiments of the present invention features of an array form synthesis regions that are for example, wells, depressions, raised regions, pins, or etched trenches. In embodiments of the invention the substrate comprises a silicon wafer or a portion of a silicon wafer. A silicon wafer may also be referred to as a chip or a semiconductor substrate. A wafer or chip may be fashioned in various shapes and sizes. The chip could be overlaid or embedded with circuitry for driving electrodes, sensing voltages, microprocessors, memory functions, and input/output capabilities. A substrate may be comprised of silicon, glass, nylon, plastic or other polymeric material, silicon nitride, metals, metal oxides, metal nitrides, or combinations thereof.

A probe or probe molecule is a small molecule or biomolecule capable of undergoing a binding or molecular recognition event with a target molecule. Molecular recognition is a specific interaction between molecules. Examples of molecular recognition events are receptor-ligand, antibody-antigen, sugar-lectin, DNA-protein, and nucleic acid hybridization reactions. A target or target molecule refers to a small molecule or biomolecule that is specifically recognized by a probe molecule through a molecular recognition event. In the case of nucleic acids, a molecular recognition event occurs when nucleic acids hybridize to complementary nucleic acids.

A hybridization reaction is a process in which two single-stranded polynucleotides bind non-covalently and form a stable double-stranded polynucleotide. In a hybridization event complementary nucleic acid bases pair up, and an adenine (A) pairs with a cytosine (C), and a guanine (G) pairs with a thymine (T) or uracil (U) (through, for example, standard Watson-Crick hydrogen-bonding interactions). Depending on conditions of pH, temperature, salt concentration, nucleic acids that are not absolutely complementary are able to hybridize. In general, substantially complementary nucleic acids refer to nucleic acids that have 80% or greater complementary base pairing. Highly complementary nucleic acids refer to nucleic acids having 90% or greater complementary base pairing. The proportion of the population of polynucleotides that forms stable hybrids is referred to as the degree of hybridization. In embodiments of the invention, hybridization refers to the formation of double stranded species between a probe polynucleotide and a target nucleic acid wherein the probe preferentially hybridizes target nucleic acids that are substantially complementary to the probe nucleic acid and does not hybridize nucleic acids that are not substantially complementary. The length chosen for a probe nucleic acid depends on several factors, including G/C content of the sequence, positioning of mismatched bases (if any), degree of uniqueness of the sequence as compared to the population of target nucleotides, the chemical nature of the polynucleotide (e.g., methylphosphonate backbone and phosphorothiolate), desired conditions for hybridization reaction (e.g., temperature and ionic strength of the solution). Typically a probe molecule will be at least 5 nucleotides and less than 75 nucleotides in length. Preferably the probe is between 24 and 60 nucleotides in length.

The term stringency refers to the conditions used for a nucleic acid hybridization reaction that influence the degree to which polynucleotides hybridize, such as pH, ion concentration, and temperature. Conditions of varying stringency can be selected that allow polynucleotide duplexes to be distinguished based on their degree of mismatch. High stringency conditions (typically higher temperature, for example), only allow the most stable duplexes to form in solution and therefore selects for hybridization reactions in which the two nucleic acids are highly complementary. Conversely, at lower stringency conditions, the probability of forming a mismatched duplex is increased. Stringency conditions that allow for selection of varying degrees of complementarity between nucleic acids are generally determined empirically. Methods for preparing, isolating, and manipulating various forms of nucleic acids are well known. (See for example, Berger and Kimmel, eds., *Guide to Molecular Cloning Techniques*, Academic Press, New York, N.Y. (1987); Sambrook, Fritsch and Maniatis, eds., *Molecular Cloning: A Laboratory Manual 2nd Ed.*, Cold Spring Harbor Press, Cold Spring Harbor, N.Y. (1989).) Additionally, techniques for hyrbidization reactions are well known and a variety of kits are commercially available for nucleic acid manipulations.

In general, nucleic acids useful in the present invention include polymers of deoxyribonucleotides (DNA) or ribonucleotides (RNA) and analogs thereof that are linked together by a phosphodiester bond. A polynucleotide can be a segment of a genome, a gene or a portion thereof, a cDNA, or a synthetic polydeoxyribonucleic acid sequence. Polynucleotides and nucleic acid polymers refer to polymeric forms of nucleotides and nucleotide analogs that comprise purine and pyrimidine bases, or other natural, chemically or biochemically modified, non-natural, or derivatized nucleotide bases, of any length. Polynucleotide and nucleic acid also refer to non-natural analogs of nucleic acids, such as peptide nucleic acids (nucleic acids with peptide backbones), and polyamide polynucleotides. An oligonucleotide is a polynucleotide having from 2 to 20 nucleotide monomer units.

A polynucleotide, including an oligonucleotide, (for example, a probe or a primer) can contain nucleoside or nucleotide analogs, or a backbone bond other than a phosphodiester bond. In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. However, a polynucleotide or oligonucleotide also can contain nucleotide analogs, including methylated nucleotides, non-naturally occurring synthetic nucleotides or modified naturally occurring nucleotides.

Typically nucleotide analogs are derived from naturally occurring nucleotides by replacing or modifying the base, the ribose, or the phosphodiester moiety. For example, structural groups can be added to the ribose or base of a nucleotide, such as a methyl, a propyl, or an allyl group at the 2'-O position of the ribose, or a fluoro group substitution at the 2-O' position. The base can also be substituted with halogens, such as bromo groups. Modified nucleotides, such as 2'-O methyloligoribonucleotides have higher affinity for complementary polynucleotides (especially RNA) than their unmodified counterparts. Additional nucleotide analogs include deazapurines and deazapyrimidines, in which one or more nitrogen atoms of the purine or pyrimidine heterocyclic ring are replaced by carbon atoms. Some examples of base modified nucleotides include 2-amonoadenine, 5-methylcytosine, 5-(propyn-1-yl) cytosine, 5-(propynl-yl)uracil, 5-bromouracil, 5-bromocytosine, hydroxymethylcytosine, methyluracil, hydroxymethyluracil, and dihydroxypentyluracil.

Some modifications tend to stabilize double-stranded DNA through the reduction of electrostatic interactions in the negatively charged phosphate backbone, or through interactions in the major or minor groove of the double helix formed by double stranded DNA. For example, adenosine and guanosine bases can be substituted at the $N^2$ position with an imidazoleyl propyl group, increasing duplex stability. Universal base analogs, such as 3-nitropyrrole and 5-nitroindole can also be used.

The covalent bond linking the nucleotides of a polynucleotide generally is a phosphodiester bond (the sugar-phosphate backbone). However, the covalent bond also can be any of a number of other types of bonds, including a thiodiester bond, an O-methyl phosphate, a phosphorothioate bond, a peptide-like amide bond or any other bond known to those in the art as useful for linking nucleotides to produce synthetic polynucleotides. The incorporation of non-naturally occurring nucleotide analogs or bonds linking the nucleotides or analogs can be particularly useful where the polynucleotide is to be exposed to an environment that can contain nucleolytic activity, since the modified polynucleotides can be less susceptible to degradation.

Probe molecule can be attached to the surface of an electronic sensor according to a variety of methods. Additionally, the electronic sensing surface may be coated with thin layers of porous materials or with conducting polymers that facilitate the attachment of probes onto the surface of the sensor. For example if the sensor is a gold electrode, a probe molecule can be attached through a thiol (—SH group) linkage.

If the sensor surface is $SiO_2$ or the surface has been coated with $SiO_2$, probes may be attached to the sensor surface through the use of silane linkers (or organo silane compounds). Silane linkers are molecules that have at least two different reactive groups bonded to the silane atom of the molecule: Y—R—Si—(X)$_2$. One of the reactive groups is capable of bonding to inorganic materials such as glass ($SiO_2$) and metals, the X group. These functional groups that are capable of bonding to inorganic materials are groups such as methoxy, ethoxy, chlorine, and silanolic hydroxyl groups. The second functional group is a group such as a vinyl, an epoxy, a methacryl, an amino, a mercapto, or a carboxylic acid group that is capable of forming a chemical bond to an organic material, the Y group. The R group is typically an organic group comprised of from 1 to 15 carbon atoms For example, a silanating agent, such as aminopropyltriethoxysilane (APTS) can be vapor deposited or supplied in a solution to the surface to be silanated. After reaction, the surface presents and amino group for further molecular coupling. Coupling can occur, for example, using glutaraldehyde and a molecular probe that presents an amine group for attachment. In another example, the surface could be silanated using carboxypropyltriethoxysilane and between a surface-attached carboxylic acid functional group and an amine or a thiol group of a molecular probe. In this case the coupling linker molecule can be 1-ethyl-3-(3-dimethylaminopropyl)-carbodiimide (EDC). Other coupling agents include N-Succinimidyl-3-maleimidopropionate (SMP), thiophosgene, and dithionite. See for example, Davis, H. D., Giannoulis, C. S., Johnson, R. W., Desai, T. A., *Biomaterials,* 23, 4019 (2002). Methods for coupling proteins to surface-attached functional groups are known and can be found in Aslam, M. and Dent, A., *Bioconjugation: Protein Coupling Techniques for the Biomedical Sciences,* Grove's Dictionaries, Inc., 301-316 (1998), for example. Metal surfaces such as nickel, palladium, platinum, titanium dioxide, aluminum oxide, indium tin oxide, copper, iridium, aluminum, titanium, tungsten, rhodium or other surface having available hydroxy groups or other similar surface groups can also be silanated for further attachment of molecules. A very thin layer of oxide can be created on a metal surface, for example, by etching the metal surface with an oxygen plasma or through damascene processes.

Nucleotides attached to a variety of functional groups may be commercially obtained (for example, from Molecular Probes, Eugene, Oreg.; Quiagen (Operon), Valencia, Calif.; and IDT (Integrated DNA Technologies), Coralville, Iowa) and incorporated into oligonucleotides or polynucleotides. Oligonucleotides may be prepared using commercially available oligonucleotide synthesizers (for example, Applied Biosystems, Foster City, Calif.). Additionally, modified nucleotides may be synthesized using known reactions, such as for example, those disclosed in, Nelson, P., Sherman-Gold, R, and Leon, R, "A New and Versatile Reagent for Incorporating Multiple Primary Aliphatic Amines into Synthetic Oligonucleotides," *Nucleic Acids Res.*, 17:7179-7186 (1989) and Connolly, B., Rider, P. "Chemical Synthesis of Oligonucleotides Containing a Free Sulfhydryl Group and Subsequent Attachment of Thiol Specific Probes," *Nucleic Acids Res.*, 13:4485-4502 (1985). Alternatively, nucleotide precursors may be obtained commercially containing various reactive groups, such as biotin, hydroxyl, sulfhydryl, amino, or carboxyl groups.

Polymeric brushes are polymers attached by one end to the surface of a substrate. Optionally, polymeric brushes comprise a functionalized polymers having functional groups such as hydroxyl, amino, carboxyl, thiol, amide, cyanate, thiocyanate, isocyanate, and isothio cyanate groups, or a combination thereof. Polymeric brushes are capable of being synthesized in a stepwise manner on the surface of the substrate and provide groups for further linking of probe molecules. Optionally, the polymeric brushes are linking molecules that link the probe molecule to the substrate.

A linker or spacer molecule typically is a molecule inserted into the growing polymer or inserted between the surface of the substrate and the probe molecule that does not necessarily convey functionality to the resulting probe, such as molecular recognition functionality, but instead elongates the distance between the substrate surface and the probe functionality to enhance the exposure of the probe functionality on the surface of the substrate. The linker molecule attaches a nucleic acid molecule to the surface and can serve to space the nucleic acid molecule above the substrate surface. Preferably a linker should be about 4 to about 40 atoms long to provide exposure of the probe molecule to the solution above the substrate surface. The linker molecules may be, for example, aryl acetylene, ethylene glycol oligomers containing 2-10 monomer units (PEGs), diamines, diacids, amino acids, among others, polypeptides and polymers of amino acid derivatives such as for example, amino hexanoic acids, and combinations thereof. Diamines are molecules of the general formula $NH_2RNH_2$, where R is a branched or unbranched hydrocarbon (a molecule composed of carbon and hydrogen) having from 2 to 45 carbon atoms, wherein one or more carbon atoms may be replaced by oxygen, sulfur, silicon, and or nitrogen atoms. Examples of diamines include ethylene diamine and diamino propane. Diacids are molecules of the general formula R'OOC—R"—COOR', where R" is a branched or unbranched hydrocarbon having from 2 to 45 carbon atoms, wherein one or more carbon atoms may be replaced by oxygen, sulfur, silicon, and or nitrogen atoms, and R' is H or a hydrocarbon having from 1 to 10 carbon atoms. Typically, the OR' groups are removed during the reactions to attach the linker molecule to the substrate surface and attach the linker molecule to the nascent polymer and the resulting linker molecule has the structure —CO—R"—CO—. Alternatively, the linkers may be the same molecule type as that being synthesized (i.e., nascent polymers), such as polynucleotides and oligonucleotides.

Optionally, the polymer brush or linker molecule comprises a cleavable group that can be cleaved with a cleaving reagent and that allows a synthesized polymer to be cleaved from the substrate surface. This cleaving reagent is a different reagent from the reagents used to remove protecting groups and the reagents used to remove protecting groups do not cause the cleavage of the cleavable group. The cleavable group provides the removal of synthesized polymers from the substrate surface in a controllable array region localized manner. Exemplary cleavable groups include acetic anhydride, n-acetylimidizole, isopropenyl formate, fluorescamine, 3-nitrophthalic anhydride, 3-sulfopropnic anhydride, and N-succinimidyl-4-[bis-(4-methoxyphenyl)-chloromethyl]-benzoate. Alternatively, polymers can be cleaved from the entire array using chemical agents, light, or heat.

Electronic detection is the detection of a molecule through a measurement of voltage, resistance, and or current characteristics of an electronic sensor in the presence of the molecules to be detected. Optionally, the electronic signal measured in the presence of the molecule to be detected is compared to an electronic signal measured in the absence of the molecules to be detected.

A wafer refers to a semiconductor substrate used in the fabrication of integrated circuits and other microdevices and is for example a substrate comprised of a silicon crystal. The wafer serves as a substrate for a microelectronic device having a large number of electronic features that is built through the use of nano and microfabrication techniques such as deposition of various materials, such as conductors, semiconductors, and insulators, photolithographic patterning, etching, and ion implantation. An array of electrodes can be equipped with circuitry for individually addressing the electrodes, driving the electrodes at selected voltages (or set current values corresponding to the desired voltage), memory for storing voltage current information to be supplied to the electrodes, memory and microprocessors for measuring electrode characteristics, differential amplifiers, field effect transistors (direct and floating gate). Alternatively, one or more of these functions can be performed by an attached computer system.

Electrode arrays are optionally used both to perform solid-phase synthesis of nucleic acids on the surface of the electrode and to detect the presence of single and double stranded nucleic acids on the surface of the electrode. For an electrode functionalized with a probe nucleic acid molecule exposed to a solution containing a target nucleic acid molecule, the presence of double stranded nucleic acids on the surface of the electrode is indicative of the occurrence of a hybridization reaction. Electronic detection provides the ability to monitor synthesis and hybridization reactions in real time without the use of labels. Since no wash is required to remove unbound labeled analytes, binding kinetics can be monitored using dynamic measurements at the solid-solution interface.

Figure 2:
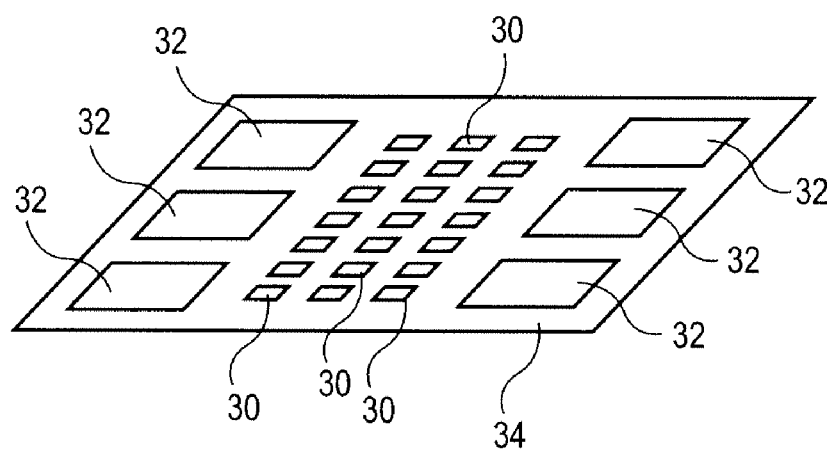
FIG. 2 is a simplified diagram of an exposed electrode array that can be used to synthesize polymers on the electrodes and to detect molecular recognition events using the array of electrodes.

FIG. 2 provides a simplified diagram showing an array of exposed sensing and reference electrodes 30 and drive electrodes 32 on a substrate 34. Nucleic acid probes (not shown) are attached to the sensing and or reference electrodes. The reference electrode may or may not have a similar or different affinity probes attached. The sensing electrodes optionally have a plurality of probe molecules attached wherein the probe molecules attached to one sensing electrode are different from the probe molecules attached to a different sensing electrode. Drive electrodes 32 are typically larger in surface area than the micron or sub-micron scale sensing and reference electrodes 30. Electronics associate with driving the electrodes and signal handling (sensing and referencing capacity) (not shown) are located in the substrate 34. An integrated charge value from an electrode is converted to a voltage value through a two stage amplifier. An internal (not exposed) monolithic NMOS or metal-insulator-metal capacitor is optionally connected to the amplifier via an internal switch and used as a reference capacitor.

Optionally, an integrating charge amplifier is connected to an electrode (or the electrodes comprising the array) and configured to detect capacitance changes at the electrode surface. A differential amplifier (or a differential-input single-ended output amplifier) is a device that amplifies the difference between two input signals (−) ad (+). Optionally, the integrating charge amplifier includes a drive circuit that is capable of providing voltage pulses which can be supplied, for example, as a square, sine, or sawtooth wave form to a solution-accessible (exposed) electrode. The integrating charge amplifier optionally also includes an input that is from an exposed sensing electrode and another input from a solution-exposed or unexposed reference electrode.

A device including one or more integrating charge amplifiers is preferably configured to measure the integrated charge and effective capacitance at the analyte-electrode interface. A change in integrated charge or effective capacitance can then be used to ascertain whether a hybridization reaction has occurred (i.e., whether analytes have bound at the electrode surface or to the affinity probe attached to the electrode surface). An array of integrating amplifiers and a corresponding electrode array are optionally fabricated on the same substrate. The substrate may also include synthesis and detection drive circuits, logic for switching, latches, memory, input/output devices.

Figure 3:
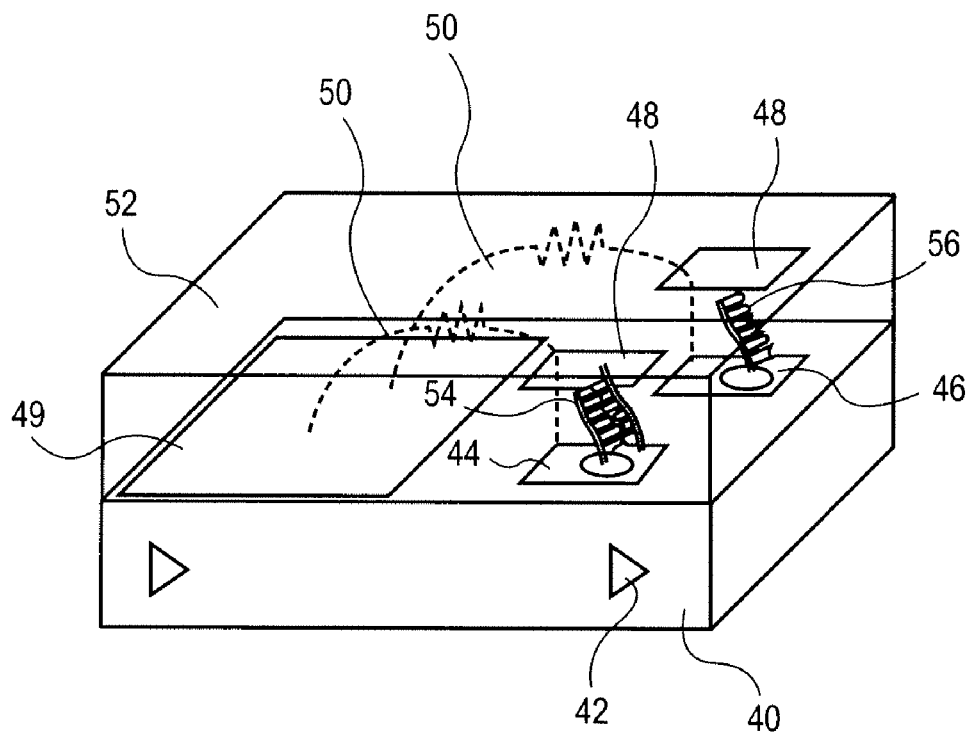
FIG. 3 provides a schematic of the electronic detection of a molecular recognition event using an array of exposed electrodes.

FIG. 3 provides a schematic of an exemplary electronic device capable of detecting a hybridization event between a surface-attached DNA probe molecule and a target molecule. The electronic molecular detection device has a substrate 40 that houses electronics for detecting 42 (as described more fully herein), exposed sensing electrodes 44, exposed reference electrode 46, and drive electrode 49. The electrodes 44, 46, and 49 are connected to electronics through physical electrical connections. In FIG. 3, dotted lines 50 demonstrate resistive and capacitive paths (virtual capacitive plates 48 are shown) established in the conductive matrix of buffer solution 52 and insulating affinity probe/analyte layer 54 on the electrode 44. The probe/analyte layer 54 is not to scale with respect to the electrode size and only one probe/analyte complex is shown (for simplicity) where many would typically be attached to an electrode surface. In FIG. 3, the electronic detection device can be operated in differential detection mode, in which both reference electrodes 46 and sensing electrodes 44 have attached affinity probes 54 and 56. The electronics 42 comprising a differential charge amplifier provide differential sensing data to an output amplifier and A/D or analog output.

For measurements of effective capacitance, the analyte is preferably provided in a conductive solution that provides a conductive path between the driving and the integrating electrodes of the amplifier. A conductive solution comprises for example, an aqueous solution having an ionic concentration or a conductive gel. A preferred method for operating a device including one or more integrating charge amplifiers includes providing a voltage pulse through the drive electrode to the conductive matrix. This pulse can be applied to the matrix with respect to an integrating electrode and the charge is accumulated on the integrating electrode over a fixed time.

Figure 4:
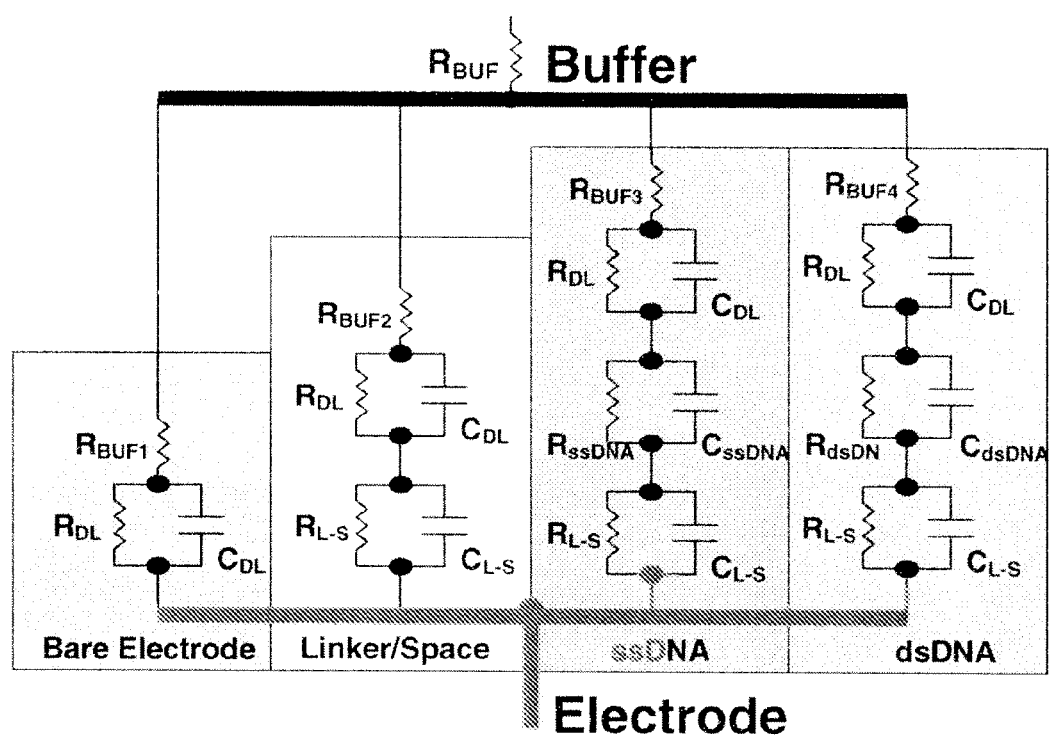
FIG. 4 shows a circuit model for the electronic detection of a molecular recognition event on an electrode.

The measured capacitance is established by the fixed sensing electrode, the dielectric formed by the attachment chemistry, attached probe, and bound analyte (if present), and a virtual parallel plate formed above the sense electrodes by the charge/ion distribution in the matrix. The measured capacitance is a function of the electrode area, the dielectric constant, and the distance of the virtual plate from the sensing electrode. Analytes binding to the electrode or the attached affinity probe will change the dielectric constant and or the distance between the virtual plate and the sensing electrode, thereby changing the effective capacitance and accumulated charge on the sensing electrode when a voltage is applied. The area and distance to the drive electrode are not material since the conductive matrix carries the voltage to the virtual plate. FIG. 4 provides a theoretical circuit model for the electronic detection of a hybridization reaction. In FIG. 4, ssDNA (single stranded DNA) represents the probe attached to the electrode and dsDNA (double stranded DNA) represents the probe hybridized to a target analyte. Any capacitance contributed by the drive electrode is in series with the measured capacitance and is small owing to the large electrode area.

Optionally, to compensate for noise that may be present (low frequency noise, thermal noise, etc.) a calibrating reference pulse is applied to an internal test capacitor to normalize the response of the amplifier during each measurement cycle. The output of this amplifier can then be digitized and post-processed. Post-processing comprises a software algorithm to remove random noise, slopes, or other artifacts from the data. Parameters can be determined experimentally by characterizing the various contributing parameters, such as electrode size, drive voltage, and environmental conditions such as temperature and analyte binding concentration.

Optionally, individually addressable sensing electrode arrays of various effective areas are created to increase the detection range of the amplifier to various concentrations of target in the solution. A large array of driving electrodes can be created to allow close coupling of driving voltage to the solution. Since the drive electrode capacitance is in series with the sense electrode plus probe or probe/target complex through the solution, preferably the driving electrode area is larger than the sensing electrode area to reduce parasitic effects. A system comprised of a large capacitor in series with a small capacitor is dominated by the small capacitor. In the case of a large capacitor in series with a small capacitor, $1/C_{series} = 1/C_{integrated} + 1/C_{drive}$ and this approaches $1/C_{integrated}$ in value as $C_{drive}$ gets large.

The exposed reference electrode allows for common mode noise rejection by inputting to one input the amplifier signal representing the same environmental conditions (pH, temperature, ion concentration, presence or absence of non-binding analytes, etc.). Alternatively, the reference capacitor can be exposed to air or covered to establish an absolute reference.

Figure 5:
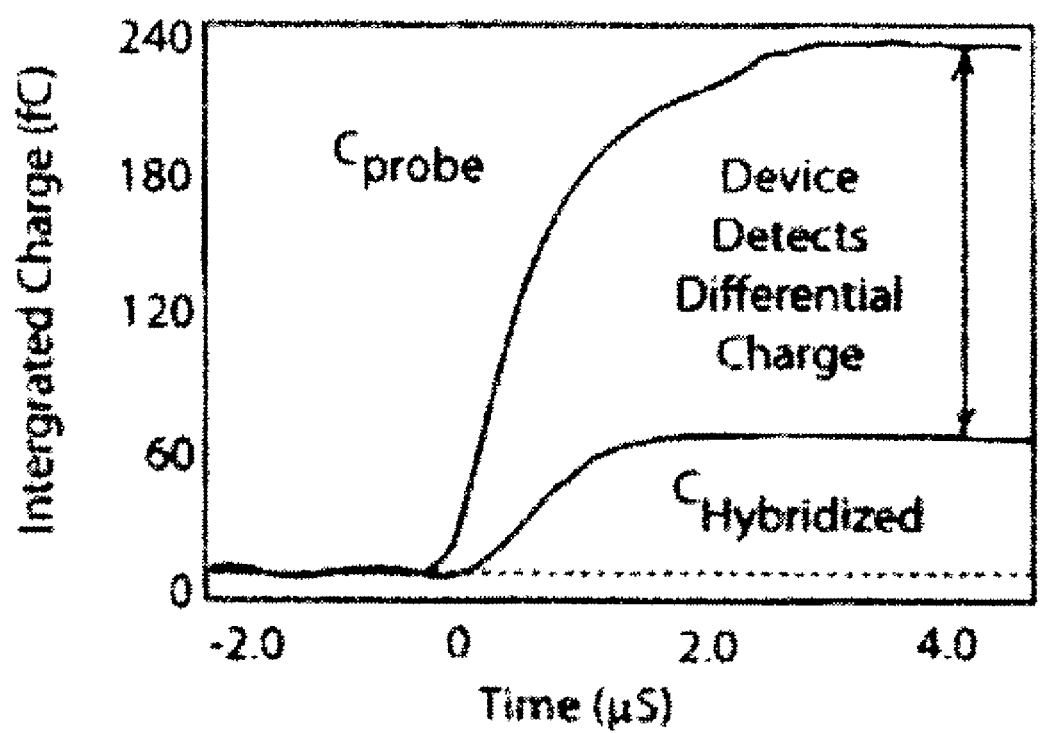
FIG. 5 provides a graph showing the electronic detection of a molecular recognition event, such as a DNA hybridization event, using exposed electrodes.

FIG. 5 provides graphs the operation of an exemplary device such as the exemplary devices shown in FIGS. 2 and 3 in the detection of a molecular recognition event at the surface of an electrode between a bound nucleic acid probe and a complementary nucleic acid molecule. FIG. 5 shows the measurement of integrated charge on two electrodes, the electrode having only the probe attached (trace labeled $C_{probe}$) and the electrode having an attached probe that is hybridized to a complementary nucleic acid (trace labeled $C_{hybridized}$). An integrating charge amplifier is used to detect capacitance on the functionalized electrode surface. A dynamic measurement at the solid-solution interface is obtained by applying a pulse to the functionalized electrode and integrating the current flow response over time as the capacitor discharges.

A pulse of voltage is applied to the solution with respect to an integrating electrode and charge is accumulated on the electrode over a fixed time. A calibrating reference pulse can be applied to the solution through an internal test capacitor to normalize the response of the amplifier during each measurement cycle. A two-stage integrating charge amplifier converts measured charge to voltage The measurement of change in capacitance at the sensing electrode can be accomplished in the following manner. The change can be detected with respect to the exposed reference capacitor when the reference electrode is exposed to the same solution as the sensing electrode. Optionally, a nucleic acid molecule that has similar electrical characteristics as the affinity probe attached to the sensing electrode but that does not bind to a target analyte in solution is attached to the reference electrode. A change in integrated charge is measured as binding occurs on the sensing electrode (binding to the probe attached on the sensing electrode) and no change is measured on the reference electrode. Alternatively, two measurements of the same electrode, before and after analyte binding, can be compared to determine the change in integrated charge resulting from target analyte binding. In this example, a measurement of the electrode at a previous time serves as the reference. Data is optionally gathered and analyzed using a computer.

In an additional alternative, the reference electrode can be configured to take direct capacitance measurements at the sensing electrode (non-differential mode). The reference electrode is covered with a dielectric substance (such as, for example, epoxy) or a dielectric layer (such as, for example, silicon dioxide) or left exposed to air. The signal from the electrode is compared to an open circuit thereby establishing an absolute reference for measurement.

The solution-accessible (or exposed) electrodes used in embodiments of the invention are made from metals, combinations of metals, or other conducting materials. For example, an electrode may be made from, for example, platinum, palladium, nickel, copper, iridium, aluminum, titanium, tungsten, gold, rhodium, as well as alloys of metals, conducting forms of carbon, such as glassy carbon, reticulated vitreous carbon, basal plane graphite, edge plane graphite, graphite, indium tin oxide, conducting polymers, metal doped conducting polymers, conducting ceramics, and conducting clays. A functionalized electrode is an electrode having a probe molecule that has a specific affinity for a target molecule attached to the electrode surface. An unfunctionalized electrode is an electrode having no probe molecule attached or an attached molecule that has no specific chemical affinity for a target molecule to be analyzed.

Electrodes are connected to sensing and driving circuitry according to known methods. For example, CMOS (complementary metal oxide semiconductor) circuitry could be used, magnetic radiation-addressable switches, direct connections from an electrode to a bond pad on the perimeter of a semiconductor chip, and or combinations thereof. Data is optionally gathered and analyzed using a computer.

Electrodes are connected to a source capable of providing voltage and current. For example, electrodes that form an array are connected to CMOS (complementary metal oxide semiconductor) switching circuitry, radio frequency (RF) and microwave addressable devices, light addressable devices, and or metal lines leading to the perimeter of the array. In embodiments of the invention, CMOS switching circuitry involves the connection of each of the electrodes to a CMOS transistor switch and provides the ability to individually address electrodes comprising an array. The switch is accessed by sending an electronic address signal down a common bus to SRAM (static random access memory) circuitry associated with the electrode. Radio and microwave frequency addressable switches involve the switching between on and off states through the use of a microwave or RF radiation. RF and microwave frequency switches can be tuned to receive a particular frequency or modulation frequency and switch without the use of array-based switching logic. Light addressable switches are moved between on and off positions by light in the ultraviolet through infra red frequency ranges. An electromagnetic signal can be spatially localized to provide switching.

Figure 6:
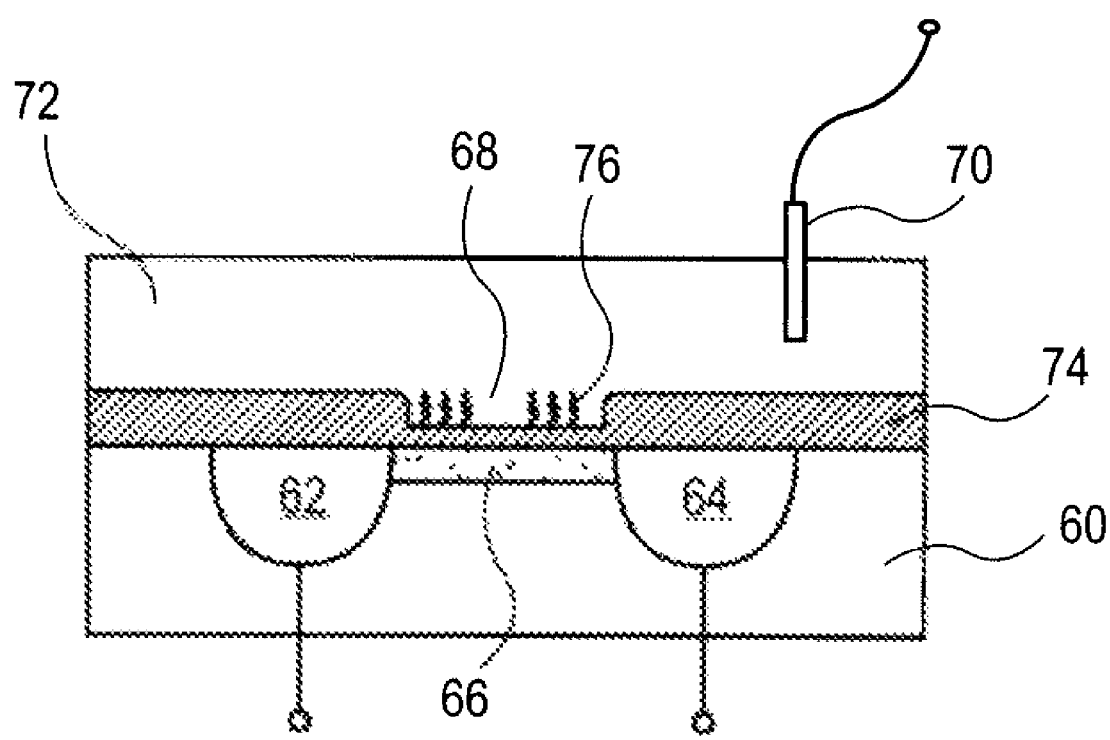
FIG. 6 provides a diagram of an exemplary field effect transistor (FET) that is capable of electronically detecting the presence of a biomolecule and the occurrence of a molecular recognition reaction.

In an additional example, an electronic sensor can be a field effect transistor (FET) or an array of FETs. FIG. 6 shows an exemplary FET device. The FET is typically constructed on a substrate 60, such as a silicon wafer and consists of a source 62 and a drain 64 connected by an active region or channel 66. A gate region 68 controls the ability of the channel 66 to conduct electrons between the source 62 and the drain 64. For the electronic detection of biomolecules, the gate region typically is a solid-solution interface and an electrode 70 is located in the solution 72 to apply a voltage between the electrolyte and the source 62. Electrons flow from the source 62 terminal to the drain 64 terminal if influenced by an applied voltage. In some examples, the channel region is covered by thin layer of an insulator 74, such as silicon dioxide, and the biomolecules 76 to be detected are attached to the surface of the thin insulating layer 74 facing the solution. A measurement of the drain current when a voltage is applied between the source and the drain and between the reference electrode and the electrolyte and the source provides information about the solution device interface where the biomolecule 76 is attached. Optionally, the surface of the insulating layer above the channel is functionalized for attachment and detection of the biomolecule with a polymer layer, linking molecule, and or spacing group. For example, the attachment of a single stranded DNA molecule to the surface proximate to the channel where the channel causes a change in the current through the channel that can be detected Such devices are known in the art and are described, for example, in "Spatially Resolved Electronic Detection of Biopolymers," *Physical Review E,* 70:031906 (2004). The channel is typically a n-type semiconductor or a p-type semiconductor. FETs can be constructed using conventional semiconductor processing techniques. A measurement device may comprise a plurality of FETs arranged in an array and capable of performing detection in a massively parallel manner. Data is optionally gathered and analyzed using a computer. A FET or a plurality of FET sensors may be integrated into a total analysis system, such as a lab-on-a-chip type device. Optionally, the reference electrode is located in the substrate 60 and in contact with the solution 72.

A region of nucleic acid molecules on an electronic detection device may be created by a variety of methods. For example, the nucleic acid molecules may be placed into a solution and spotted onto the surface of the electronic detection device. Spotting systems that allow a plurality of solutions to be spotted onto an array in a controlled manner are commercially available, form for example, Agilent Technologies, Santa Clara, Calif. For example, the spotting is accomplished using a plurality of micro pipets.

An array of nucleic acid can also be created using in situ synthesis methods. For example, the synthesis of an array of nucleic acid molecules on a substrate can be accomplished using photochemical synthesis methods, photoresist synthesis methods, and electrochemical synthesis methods. In photochemical synthesis techniques, protecting groups that prevent polymer growth are removed photochemically.

In photoresist synthesis methods, a photoresist is applied over the array synthesis area and the photoresist is patterned with electromagnetic radiation to expose areas in which the polymer chain is to be extended by monomer addition or to protect regions in which the polymer chain is not to be extended from monomer addition. In an exemplary synthesis method, photoresists such as poly(methyl methacrylate) (PMMA) are provided with sulfonium, polonium, or halonium salts that generate an acid upon exposure to UV light. The photo-chemically generated acid deprotects the protected polymer chain (for example, through the removal of a DMT group) to allow the addition of a monomer to the growing end of the unprotected polymer chain. Optionally, the photoresist layer also includes a photosensitizer, such as a benzophenone, a thioxanthenone, an anthraquinone, a fluorenone, an acetophenone, or perylene. In the case of a photosensitizer, the generation of the protecting group removal reagent may occur through the absorption of light by a photosensitizer followed by reaction of the photosensitizer with the protecting group removal reagent precursor (the molecule capable of generating an acid upon activation), energy transfer from the photosensitizer to the cleavage reagent precursor, or a combination of two or more different mechanisms. After the photoresist is removed, the polymer chain in the light-exposed regions is available for monomer addition. Through repeated cycles of photoresist coating, light exposure (optionally through a mask to pattern the photoresist), and monomer addition, an array of polymers is built on the surface of a substrate.

Figure 7:
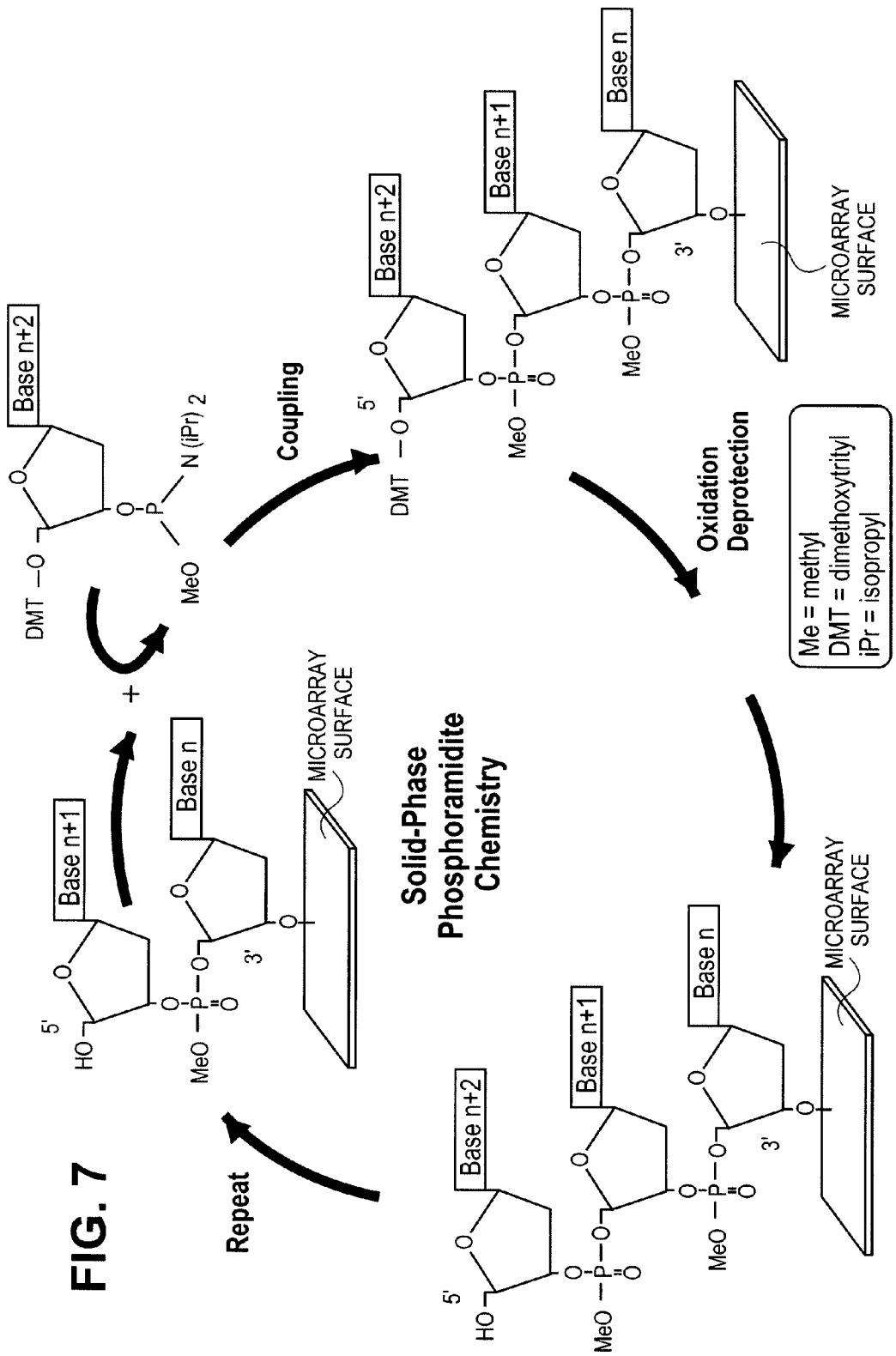
FIG. 7 diagrams a method for solid-phase nucleic acid synthesis that can be used to controllably build nucleic acid molecules having a desired sequence on a solid surface.

A monomer addition cycle is a series of chemical reactions that result in the addition (or covalent attachment) of a monomer to a growing polymer chain or linker molecule. For example, the following steps typically comprise a common method used to synthesize a polynucleotide on a solid support (i.e., phosphoramidite-based solid phase polynucleotide synthesis). Referring now to FIG. 7, a first step in the polynucleotide synthesis is the deprotection of the surface-attached polymer growth site through removal of the DMT group from, for example, a 5'-protected nucleotide wherein the 5'-hydroxyl is blocked through the covalent attachment of DMT. The deprotection is accomplished using a protic acid (for example, a protic acid such as trichloroacetic acid, dichloroacetic acid, or an electrochemically generated acid). The substrate optionally is then washed to remove the cleaved protecting group and other reagents and mobile reaction products (with, for example, acetonitrile). A molecule, such as a phosphoramidite nucleotide, optionally activated with tetrazole, is then coupled to the surface-attached deprotected molecule. Optionally unreacted surface-attached deprotected molecules are capped to prevent further participation in subsequent monomer addition cycles. The trivalent phosphate trimester linkage is converted to a pentavalent phosphate triester through oxidation with, for example, iodine, and the pentavalent phosphate triester is converted to a phosphodiester through reaction with ammonium hydroxide.

Electrochemical reagents are reactive species that can be generated electrochemically at an electrode through an oxidation or reduction process. Electrochemical reagents can be generated at an electrode by supplying a minimum voltage that corresponds with the oxidation or reduction potential of the desired species in solution. Exemplary electrochemical reagents that are oxidants include iodine, bromine, chlorine, iodate, periodic acid, hydrogen peroxide, hypochlorite, metavanadate, bromate, dichormoate, cerium (IV), and permanganate species. Exemplary reductants that can be generated electrochemically include chromium (II), ferrocyanide, thiols, thiosulfate, titanium (III), arsenic (III), and iron (I) species. Additionally, species such as acids ($H^+$) and bases (such as $OH^-$) can be generated electrochemically. Molecules that can be used to generate an acid electrochemically that can used to deprotect a growing nucleic acid polymer attached to an electrode surface (e.g., remove a DMT group) include, for example hydroquinone that is converted to benzoquinone upon oxidation thereby releasing two protons ($H^+$) and a hydroquinone that is converted to anthraquinone upon oxidation thereby releasing two protons ($H^+$) (a non-aqueous system).

A protecting group is a chemical functional group that is designed to block a reactive site in a molecule, but that may be removed upon exposure to an activator or a deprotecting reagent. When the protecting group is removed, the reactive site is more readily available to react and form chemical bonds. A deprotecting agent is an agent that can remove a protecting group from a molecule leaving the reactive site available for further chemical reaction. Deprotecting reagents include, for example, acids, bases, free radicals, and electromagnetic radiation. Protecting groups can be bound to a monomer, a polymer, a linker molecule or a monomer, or polymer, or a linker molecule attached to a solid support to protect a reactive functionality on the monomer, polymer, or linker molecule. Hydroxyl groups on phosphoramidites may be protected by dimethoxytrityl (DMT), which is acid labile (removable). Exocyclic amine groups on nucleotides, in particular on phosphoramidites, are preferably protected by dimethylformamidine on the adenosine and guanosine bases, and isobutyryl on the cytidine bases, both of which are base labile protecting groups. This protection strategy is sometimes known as fast oligonucleotide deprotection (FOD).

Any unreacted deprotected chemical functional groups may be capped at any point during a synthesis reaction to avoid or to prevent further bonding at the selected molecule. In general, capping reagents are agents that prevent further chain growth at the site of polymer chain formation such as, for example, an acid anhydride without further reactive functionalities. Capping groups cap deprotected functional groups by, for example, binding with the unreacted amino functions to form amides. Capping agents suitable for use in an embodiment of the invention include: acetic anhydride, n-acetylimidizole, isopropenyl formate, fluorescamine, 3-nitrophthalic anhydride and 3-sulfoproponic anhydride.

An electrochemical reagent is a species in solution that is generated at a solution-accessible electrode by applying sufficient electrical potential to an electrode. The electrochemical reagent is capable of removing a protecting group from the growing end of a polymer being synthesized on the electrode. In this instance the electrochemical reagent is a deprotecting agent. In other reactions, the electrochemical reagent may be an intermediate in the formation of the deprotecting agent.

The electrodes of the array optionally are also used to synthesize polymers. For synthesis the electrodes are used to create an acidic or basic region around the electrode surface. The acid or base causes deprotection of the growing polymer chain and allows monomer addition. Optionally, confinement electrodes of opposite polarity or floating separate attachment electrodes are provided to confine the acid or basic region produced and prevent drift to surrounding electrodes that may not be activated for synthesis. Further optionally, a set of two latches are provided at each electrode capable of being activated for polymer synthesis to allow the electrode to exist in multiple states: driven by a first voltage, driven by a second voltage, or floated during the synthesis cycle.

Voltage sources for the electrodes can be internally multiplexed from external source(s) through digital control and can optionally be applied in parallel to a large array of electrodes.

In operation, voltages are applied to a programmed selection of electrodes as a solution containing a monomer is supplied to the exposed electrodes. An applied voltage creates an acidic or basic region and allows polymer growth at the selected electrode. Through selection of electrodes and choice of monomer to supply, polymers of known desired sequence are synthesized at the electrodes.

A wide range of useful fluorescent dyes, label molecules, and label constructs are known. These molecules can be attached to nucleotides and incorporated into DNA molecules. Exemplary fluorescent label molecules include, xanthene dyes, fluorescein, lissamine, phycoerythrin, rhodamine dyes, coumarin dyes, and cyanine dyes (cy3, cy5, cy7, etc.). Examples of label constructs include, Q dots, metal nanoparticles, and Raman reporter particles. Raman reporter particles are metal nanoclusters having an organic molecule absorbed on or within the metal cluster or particle where the organic molecule capable of providing a unique Raman signature. The metal cluster provides a surface for enhancing the Raman signal, and the metal nanocluster provides an intrinsic surface enhanced Raman signal (SERS) from the organic molecule absorbed on or within the cluster. A variety of labeled nucleotides are commercially available from, for example, Jena Bioscience, Jena Germany. Intrinsically fluorescent nucleotide analogs are also possible. Fluorescently labeled nucleotides and fluorescent nucleotides can be incorporated into DNA polymers and oligonucleotides through PCR techniques (polymerase chain reaction).

A fluorescent label molecule or SERS signal is detected using known methods for spectroscopy. Typically ultraviolet light is used to excite the fluorescent label molecule and the fluorescent molecule emits light at a lower energy (sometimes visible light), and the emitted light is detected. The excitation light can be provided by lasers, photodiodes, xenon arc lamps, or mercury vapor lamps. Optics are used to focus the light onto a detector and filter excitation light from emitted light. A monochromator may be used in conjunction with the detector to scan through wavelengths of light. Microarray fluorescence readers are commercially available from, for example, Perkin Elmer Corporation, Waltham, Mass. and Applied Precision, Issaquah, Wash. Raman spectrometers are commercially available from, for example, Perkin Elmer Corporation, Waltham, Mass.

What is claimed is:

1. A method for detecting a molecular recognition event comprising,
    providing a substrate having a surface wherein the surface has an array of electronic detectors wherein the electronic detectors are comprised of at least one drive electrode, at least one sensing electrode, and at least one reference electrode, wherein the at least one drive electrode is connected to both drive circuitry configured to drive polymer synthesis and an integrating charge amplifier, wherein a surface area of a drive electrode is larger than a surface area of a reference electrode, and wherein first nucleic acid molecules are attached to the surface of a sensing electrode;
    providing second nucleic acid molecules under conditions that allow the second nucleic acid molecules to hybridize to the first nucleic acid molecules wherein the second nucleic acid comprises two regions: one region that is substantially complementary to the first nucleic acid molecule and a second region that is not substantially complementary to the first nucleic acid molecule and wherein the second region that is not substantially complementary remains single stranded and available for further hybridization reactions after the first hybridization reaction with the first nucleic acid molecule;
    electronically detecting the hybridization reaction between the first and second nucleic acid molecules using the electronic detectors;
    providing third nucleic acid molecules that are substantially complementary to the second region of the second nucleic acid molecule under conditions that allow the third nucleic acid molecules to hybridize to the second region of the second nucleic acid molecule wherein the third nucleic acid molecules comprise an optically detectable label; and
    optically detecting the label of the third nucleic acid molecules.

2. The method of claim 1 wherein the array contains 1,000 to 10,000 electrodes.

3. The method of claim 1 wherein the array contains 100 to 1,000 electrodes.

4. The method of claim 1 wherein a feature size of the array is less than 100 $\mu m^2$.

5. The method of claim 1 wherein electronically detecting the hybridization reaction comprises detecting a capacitance change on the sensing electrode surface.

6. The method of claim 5 wherein the capacitance change is detected using an integrating charge amplifier.

7. The method of claim 1 wherein at least one electrode is comprised of platinum, palladium, nickel, copper, iridium, aluminum, titanium, tungsten, gold, rhodium, glassy carbon, conducting graphite, or combinations thereof.

8. The method of claim 1 wherein at least one electrode is comprised of platinum or palladium.

9. The method of claim 1 wherein the label comprises a fluorescent molecule.

10. The method of claim 1 wherein the label comprises an optically detectable nanoparticle.

11. The method of claim 1 wherein the nucleic acid molecules attached to the surface of the electronic detectors were synthesized on the electronic detectors.

12. The method of claim 1 wherein the nucleic acid molecule is attached to the surface of the electronic detector through a linker molecule.

13. The method of claim 12 wherein the linker molecule is selected from the group consisting of aryl acetylenes, polyethyleneglycols, diamines, diacids, polynucleotides, and combinations thereof.

14. The method of claim 1 wherein the third nucleic acid molecule is highly complementary to the second region of the second nucleic acid molecule.

15. The method of claim 1 also including removing any unhybridized third nucleic acid molecule before optically detecting the label of the third nucleic acid molecule.

* * * * *